(12) United States Patent
Rojas Martinez et al.

(10) Patent No.: US 9,783,832 B2
(45) Date of Patent: Oct. 10, 2017

(54) **METHOD FOR PRODUCING 2,3-BUTANEDIOL USING IMPROVED STRAINS OF *RAOULTELLA PLANTICOLA***

(71) Applicants: BIOPOLIS, S.L., Paterna (ES); UNIVERSIDAD COMPLUTENSE DE MADRID, Madrid (ES)

(72) Inventors: Antonia Maria Rojas Martinez, Valencia (ES); Silvia Segarra Manzano, Valencia (ES); Alejandro Montesinos Paes, Torrent (ES); Marta Tortajada Serra, Valencia (ES); Daniel Ramon Vidal, La Eliana (ES); Victoria Eugenia Santos Mazorra, Madrid (ES); Miguel Ladero Galan, Madrid (ES); Felix Garcia-Ochoa Soria, Pozuelo de Alarcón (ES); Vanessa Ripoll Morales, Madrid (ES); Alberto Rodriguez Martín, Las Rozas (ES)

(73) Assignees: Biopolis, S.L. (ES); Universidad Complutense de Madrid (ES)

( * ) Notice: Subject to any disclaimer, the term of this patent is extended or adjusted under 35 U.S.C. 154(b) by 0 days.

(21) Appl. No.: 14/415,343

(22) PCT Filed: Jul. 22, 2013

(86) PCT No.: PCT/IB2013/001592
§ 371 (c)(1),
(2) Date: Jan. 16, 2015

(87) PCT Pub. No.: WO2014/013330
PCT Pub. Date: Jan. 23, 2014

(65) Prior Publication Data
US 2015/0191752 A1  Jul. 9, 2015

(30) Foreign Application Priority Data

Jul. 17, 2012 (ES) .................................. 201231119

(51) Int. Cl.
| | | |
|---|---|---|
| *C12P 7/18* | (2006.01) | |
| *C12R 1/00* | (2006.01) | |
| *C12R 1/22* | (2006.01) | |
| *C12N 1/20* | (2006.01) | |
| *C12N 1/32* | (2006.01) | |
| *C12R 1/01* | (2006.01) | |
| *C12N 15/01* | (2006.01) | |

(52) U.S. Cl.
CPC .................. *C12P 7/18* (2013.01); *C12N 1/20* (2013.01); *C12N 1/32* (2013.01); *C12N 15/01* (2013.01); *C12R 1/01* (2013.01)

(58) Field of Classification Search
CPC .................. C12P 7/18; C12R 1/00; C12R 1/22
See application file for complete search history.

(56) References Cited

U.S. PATENT DOCUMENTS

| 5,254,467 A | * | 10/1993 | Kretschmann | ............ | C12P 7/18 435/158 |
| 2014/0342419 A1 | * | 11/2014 | Dischert | ................ | C12N 15/52 435/158 |

FOREIGN PATENT DOCUMENTS

| JP | WO 2008126667 A2 | * | 10/2008 | ................ | C12P 7/56 |
| JP | WO 2008126669 A2 | * | 10/2008 | ................ | C12P 7/40 |
| JP | 2010-226959 A | * | 10/2010 | ................ | C12N 1/20 |
| KR | 2012-0096756 A | * | 8/2012 | ................ | C12N 1/20 |

OTHER PUBLICATIONS

Sanchez, M., et al., 2005, "Klebsiella planticola strain DSZ mineralizes simazine: physiological adaptations involved in the process", Appliws Microbiology and Biotechnology, vol. 66, pp. 589-596.*
Jarvis, G.N., et al., 1997, "Formate and ethanol are the major products of glycerol fermentation produced by a Klebsiella planticola strain isolated from red deer", Journal of Applied Microbiology, vol. 83, pp. 166-174.*
Machine translation of JP 2010-116959, 27 pages.*
Machine translation of KR 2012-0096756, 7 pages.*
Kaloyan Petrov et al., "High production of 2,3-butanedioi from glycerol by Klebsiella pneumoniae G31", Appl Microbiol Biotechnol, 2009, pp. 659-665, vol. 84.
Kaloyan Petrov et al., "Enhanced production of 2,3-butanediol from glycerol by forced pH fluctuations", Appl Microbiol Biotechnol, 2010, pp. 943-949, vol. 87.
Soojin Lee et al., "Synthesis of Pure meso-2,3-Butanediol from Crude Glycerol Using an Engineered Metabolic Pathway in *Escherichia coli*", Appl Biochem Biotechnol, 2012, pp. 1801-1813, vol. 166.
H. Biebl et al., "Fermentation of glycerol to 1,3-propanediol and 2,3-butanediol by Klebsiella pneumoniae", Appl Microbiol Biotechnol, 1998, pp. 24-29, vol. 50.
Pablo H. Cueto et al., "Direct Selection of Clostridium acetobutylicum Fermentation Mutants by a Proton Suicide Method", Applied and Environmental Microbiology, 1990, pp. 578-580, vol. 56, No. 2.
International Search Report of PCT/IB32013/001592 dated Feb. 3, 2014 [PCT/ISA/210].

* cited by examiner

*Primary Examiner* — Kagnew H Gebreyesus
(74) *Attorney, Agent, or Firm* — Hayes Soloway PC

(57) ABSTRACT

The invention relates to a method for producing 2,3-butanediol using improved strains of *Raoultella planticola*, and to novel mutant strains obtained by random mutagenesis from the bacterial species *Raoultella planticola* CECT843, that can be used in the industrial production of 2,3-butanediol from glycerol. The invention preferably relates to the *Raoultella planticola* strains designated IA1 and IIIA3 and deposited in the Spanish Type Culture Collection (CECT) under deposit number CECT8158 (corresponding to the strain designated IA1) and deposit number CECT8159 (corresponding to the strain designated IIIA3). The invention also relates to a method for producing 2,3-butanediol from glycerol by means of a biotechnological process using the novel strains of the invention.

13 Claims, 3 Drawing Sheets

A

B

A.

B.

METHOD FOR PRODUCING 2,3-BUTANEDIOL USING IMPROVED STRAINS OF *RAOULTELLA PLANTICOLA*

CROSS REFERENCE TO RELATED APPLICATIONS

This application is a National Stage of International Application No. PCT/IB2013/001592, filed Jul. 22, 2013, claiming priority based on Spanish Patent Application No. 201231119, filed Jul. 17, 2012, the contents of all of which are incorporated herein by reference in their entirety.

TECHNICAL FIELD OF THE INVENTION

The present invention relates to novel mutant strains obtained by random mutagenesis from the bacterial species *Raoultella planticola* CECT843 that can be used in the industrial production of 2,3-butanediol from glycerol. The present invention preferably relates to the *Raoultella planticola* strains designated IA1 and IIIA3 and deposited in the Spanish Type Culture Collection (CECT) under deposit number CECT8158 (corresponding to the strain designated IA1) and deposit number CECT8159 (corresponding to the strain designated IIIA3). The present invention also relates to a method for producing 2,3-butanediol from glycerol by means of a biotechnological process using the novel strains of the invention.

BACKGROUND OF THE INVENTION

Using byproducts to produce biofuels, energy and basic chemical compounds is increasingly more needed in the current oil shortage situation. Many compounds that have conventionally been produced from oil can be biotechnologically synthesized today using renewable resources. This is the case of biologically producing 2,3-butanediol.

2,3-butanediol is an organic compound, specifically an alcohol, the molecular formula of which is $C_4H_{10}O_2$. There are three isomeric forms thereof: D-(−)-, L-(+)- and meso-, and it is also known as 2,3-butylene-glycol, dimethyleneglycol, dimethylethylene-glycol, and its name according to IUPAC is butane-2,3-diol. Its molecular weight is 90.121 (g mol$^{-1}$), and it is found in cocoa butter and in the roots of the plant called *Ruta graveolens*.

Interest in this compound has increased considerably in recent years due to the large number of industrial applications it has, primarily in the chemical and energy industry. Both 2,3-butanediol and some of its derivatives are used in the production of plastics and solvents. Given its high octane rating, 2,3-butanediol is useful as an octane enhancer in fuels. Given its low melting point (−60° C.), it is also used as antifreeze. As an analytical reagent, 2,3-butanediol is used for resolving carbonyl compounds in gas chromatography.

One of the main applications of 2,3-butanediol is its conversion into 1,3-butadiene, which is used for synthetic rubber production. In addition, the 2,3-butanediol dehydrogenation product, diacetyl, is a highly valued bacteriostatic flavoring agent in the food industry. 2,3-butanediol dehydration yields methyl ethyl ketone (MEK), which is an additive with high combustion heat used in fuels. MEK is also used as a resin and lacquer solvent. Polyurethane-melamides (PUMAs), which are useful in cardiovascular applications, are obtained from 2,3-butanediol esterification with malic acid. Other 2,3-butanediol esterification products are used in cosmetics and in the pharmaceutical industry. Finally, the production of wetting agents, elastane, fumigants, plasticizers (such as polyvinyl chloride, cellulose nitrate and polyacrylates, for example), perfumes, printing inks, softeners and drug vectors are also considered potential applications of 2,3-butanediol.

Various microorganisms are capable of accumulating 2,3-butanediol, such as, for example, strains of the bacterial species *Aeromonas hydrophila, Aerobacter indologenes, Bacillus amyloliquefaciens, Bacillus licheniformis, Bacillus polymyxa, Bacillus subtilis, Brevibacillus brevis* S1, *Corynebacterium glutamicum, Enterobacter aerogenes, Enterobacter cloacae, Klebsiella pneumoniae, Klebsiella oxytoca, Klebsiella terrigena, Lactobacillus brevis, Lactobacillus casei, Lactobacillus helveticus, Lactobacillus plantarum, Lactococcus lactis, Lactococcus lactis* subsp. *lactis* var. *diacetylactis, Leuconostoc lactis, Leuconostoc mesenteroides* subsp. *cremoris, Oenococcus oeni, Pediococcus pentosaceus, Pseudomonas chlororaphis, Raoultella terrigena, Serratia marcescens, Streptococcus faecalis*, some rhizobacteria and marine algae *Chlamydomonas perigranulata*, although not all of them do so in significant amounts. Some yeasts are also capable of synthesizing 2,3-butanediol, but with very low productivity, so the only microorganisms of industrial importance for production of this compound are bacteria.

It is furthermore known that 2,3-butanediol synthesis seems to play a very important physiological role for microorganisms as it prevents acidification, regulates the NADH/NAD$^+$ ratio and stores carbon and energy for growth. The genes responsible for 2,3-butanediol conversion from *A. aerogenes* and *K. terrigena* have been cloned and characterized. They are an operon called budABC consisting of three genes encoding three key enzymes: α-acetolactate synthase, α-acetolactate decarboxylase and acetoin reductase (2,3-butanediol dehydrogenase).

The bacteria identified up until now as the most efficient among 2,3-butanediol producers are *B. polymyxa, K. oxytoca* and *K. pneumoniae*, and they primarily use sugars as a substrate.

In addition, it is well known that the ideal solution in base chemical compound production is the bioconversion of industrial byproducts (such as glycerol, whey or agricultural waste) or the use of excess biomass (such as wood hydrolysate). Particularly, and given that about 100 Kg of crude glycerol are generated per ton of product in biodiesel production, and taking into account the increase in biodiesel production, finding alternatives for later use of this byproduct is of interest. For this reason, glycerol is known as one of the potentially most interesting substrates for producing 2,3-butanediol.

In the fermentation processes for converting glycerol into products other than 2,3-butanediol, such as 1,3-propanediol, the participation of several strains belonging to the species *K. pneumoniae*, for example, the *K. pneumoniae* strain DSM 2026, which is a very good glycerol fermenter, stands out. In turn, *K. pneumoniae* strain G31 is better under fermentation conditions in which the pH value is not controlled.

These species are also capable of producing 2,3-butanediol from glycerol. In batch feed fermentation processes, *K. pneumoniae* G31 produced 2,3-butanediol with a yield of 0.36 g/g (Petrov & Petrova, 2009)[6], and in assays with forced pH variations, the yield was 0.39 g/g, produced from glycerol in both cases (Petrov & Petrova, 2010)[7]. However, species *K. pneumoniae* is classified as a group 2 biological agent, which means that it is a pathogenic agent that can cause diseases in humans and be a risk for workers (Directive 2000/54/CE of the European Parliament and of the Council of 18 Sep. 2000), so strains of this species are not suitable for use in industrial biotechnology.

With respect to patent documents, patent document U.S. Pat. No. 5,254,467 relates to a process for the conversion of glycerol into 1,3-propanediol by means of microorganisms. Said process comprises fermenting said microorganisms in a medium containing 5-20% by weight of glycerol under standard anaerobic fermentation conditions, subsequently recovering the produced 1,3-propanediol, and 2,3-butanediol as a secondary product. The patent document mentions *Klebsiella planticola* strain IAM 33 as a possible microorganism useful for these purposes. Nevertheless, the 2,3-butanediol production yield in this fermentation process is very low so use thereof is not feasible on an industrial level.

Patent document JP 2010226959 discloses the use of other microorganisms with the ability to generate ethanol from glycerol, specifically *Raoultella ornithinolytica* and *R. planticola*, even though it does not mention producing 2,3-butanediol.

The object of patent document US2007/0148749 A1 is to improve 1,3-propanediol production from glycerol using certain bacteria strains belonging to genera *Caloramator, Citrobacter, Clostridium, Enterobacter, Escherichia, Klebsiella, Lactobacillus, Listeria* and *Salmonella* using a reaction catalyzed by enzymes in which the first step is converting glycerol into 3-hydroxypropionaldehyde and water, and the second step is reducing 3-hydroxypropionaldehyde to 1,3-propanediol. It does not mention producing 2,3-butanediol.

The object of the invention of patent document US 2008/0274522 A1 is a method for the 2-butanone production by means of fermentation by a microorganism. The method uses the enzyme acetolactate synthase and temperature reduction during the fermentation process, resulting in higher tolerance of the host to butanone. It does not mention producing 2,3-butanediol.

Patent application WO 2007/130518 A2 relates to 2-butanol production by means of the industrial fermentation of a recombinant microorganism. The transgenic host contains at least one recombinant DNA molecule containing a gene encoding a polypeptide with the ability to catalyze a substrate and to perform conversion of: i) pyruvate into alpha-acetolactate; ii) alpha-acetolactate into acetoin; and iii) acetoin into 3-amino-2-butanol. It does not mention producing 2,3-butanediol.

Patent document EP 1892300 A1 provides a method for producing 1,3-propanediol starting from crude glycerol, a byproduct obtained during biodiesel production, and using as fermentation microorganisms *Clostridium butyricum, Clostridium pasteurianum* and *Klebsiella pneumoniae*. It does not mention producing 2,3-butanediol.

All the other significant examples of producing 2,3-butanediol refer to the use of sugars (e.g. glucose) as a substrate.

Therefore, the technical problem of the present invention relates to providing novel strains of the species *R. planticola*, that can be used in the industrial production of 2,3-butanediol from glycerol. Said technical problem is preferably resolved by providing two novel strains of *R. planticola* designated in the present description as IA1 and IIIA3 and deposited on Dec. 6, 2012 with accession number CECT8158 (corresponding to IA1) and accession number CECT8159 (corresponding to IIIA3) in the Spanish Type Culture Collection (CECT), Parc Cientific Universitat of Valencia, c/Catedrático Agustín Escardino, 9, 46980 Paterna—Valencia, Spain, according to the provisions of the Budapest Treaty. Said strains have a 2,3-butanediol production capacity that is better than other strains in the same species, so the present invention also contemplates an industrially viable method for the biotechnological conversion of glycerol into 2,3-butanediol using said novel strains or mutants thereof.

OBJECT OF THE INVENTION

The present invention relates to novel strains of the species *R. planticola*, obtained by random mutagenesis from *R. planticola* strain CECT843. Specifically, the present invention relates to *R. planticola* strains CECT8158 and CECT8159 which have a 2,3-butanediol production capacity that is better than wild-type species and other strains of the same species, as well as to providing an industrially viable method for the biotechnological conversion of glycerol into 2,3-butanediol using any of said novel strains or mutants thereof.

Another object of the present invention relates to a method for producing strains of the species *R. planticola*, particularly those deposited as CECT8158 and CECT8159, obtained through randomly induced mutagenesis of wild-type strain CECT843 and subsequent forced selection of mutants in bromate/bromide plates with an improved 2,3-butanediol production capacity.

Another object of the present invention relates to a method for producing 2,3-butanediol, comprising the following steps:
a) aerobically fermenting the microorganism *R. planticola* strains CECT8158 or CECT8159 capable of converting glycerol into 2,3-butanediol in a medium comprising an aqueous solution with a glycerol content of at least 3% by weight, preferably 6% by weight, under conditions suitable for producing 2,3-butanediol; and
b) a process for separating the 2,3-butanediol produced from the reaction medium.

Yet another object of the present invention relates to defining the optimal reaction parameters during fermentation for producing 2,3-butanediol using the novel *R. planticola* strains of the present invention in a batch fermentation system.

Another object of the present invention relates to a novel biotechnological method for producing 2,3-butanediol attaining an optimal conversion yield of 40-50% by weight (g 2,3-butanediol/g glycerol consumed), preferably 30% more with respect to the yield obtained using the wild-type strain.

Finally, another object of the present invention relates to providing a method for producing 2,3-butanediol from glycerol in a fermentation process, both pure glycerol and industrial (crude) glycerol, which is generated in the biofuel industry as a byproduct of biodiesel production processes, being able to be applied as a carbon source for the purpose of the present invention.

DETAILED DESCRIPTION OF THE INVENTION

Figure 1:
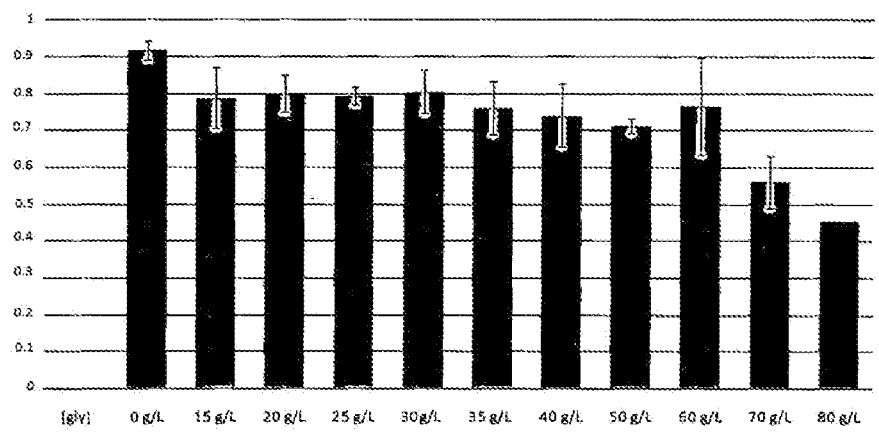
FIG. 1A shows growth of *R. planticola* strain CECT843 in increasing concentrations of glycerol. The average results of four replicas are illustrated.
FIG. 1B shows growth of *K. oxytoca* strain m5a1 in increasing concentrations of glycerol. The average results of four replicas are illustrated.
Figure 1:
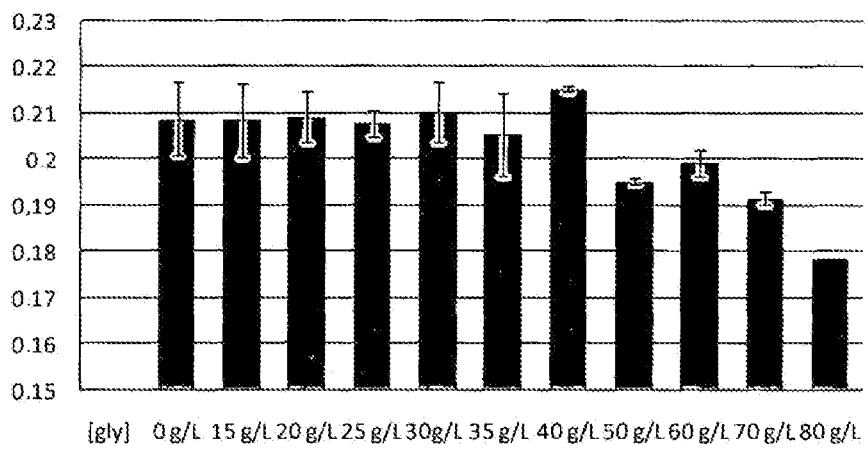

The present invention relates to novel strains of species *R. planticola*, obtained by random mutagenesis from *R. planticola* strain CECT843. The present invention specifically relates to *R. planticola* strains CECT8158 and CECT8159, which have a 2,3-butanediol production capacity that is better than wild-type species and other strains of the same species, as well as to providing an industrially viable method for the biotechnological conversion of glycerol into 2,3-butanediol using any of said novel strains or mutants thereof, comprising the following steps:

a) aerobically fermenting the microorganism *R. planticola* strains CECT8158 or CECT8159 capable of converting glycerol into 2,3-butanediol in a medium comprising an aqueous solution with a glycerol content of at least 3% by weight, preferably 6% by weight, under conditions suitable for producing 2,3-butanediol; and b) a process for separating the 2,3-butanediol produced from the reaction medium.

For the purpose of the present invention, conversion efficiency in the method for producing 2,3-butanediol fundamentally depends on the selection of microbial strains with a high 2,3-butanediol production capacity, as well as a high capacity for growth and viability in a culture medium with high concentrations of glycerol and 2,3-butanediol.

I. Selection of *R. planticola* Strain CECT 843 a) Identification and Isolation of 2,3-butanediol Producer Microorganisms

A collection of 2,3-butanediol producer strains from glycerol was established, using the following collection strains: *Raoultella terrigena* CECT 4519, *Pantoea agglomerans* CECT 4842, *Paenibacillus polymyxa* CECT 155-T, *Paenibacillus polymyxa* CECT 153, *Paenibacillus polymyxa* DSM 356, *Paenibacillus polymyxa* ATCC 12321, *Paenibacillus xylamilyticus* CECT 5839-T, *Bacillus licheniformis* CECT 4536, *Bacillus licheniformis* DSM8785, *Bacillus licheniformis* TUL, *Bacillus subtilis* TUL322, *Bacillus amyloliquefaciens* TUL, *R. planticola* CECT 843, *R. planticola* IAM 1133 (NCIMB 8153), *Escherichia blattae* ATCC 33430, *Klebsiella oxytoca* m5a1, *Klebsiella oxytoca* NRRL-B199, *Bacillus aquimaris* BPCOIN34, *Bacillus flexus* BPCOIN20, *Bacillus megaterium* BPCOIN39, *Bacillus marinus* BPCOIN33, *Bacillus murimartini* BPCOIN2, *Bacillus murimartini* BPCOIN7, *Bacillus pumilus* BPCOIN1, *Bacillus pumilus* BPCOIN21, *Bacillus silvestris* BPCOIN24, *Bacillus silvestris* BPCOIN22, *Bacillus thuringiensis* BPCOIN23, *Bacillus thuringiensis* BPCOIN61, *Bacillus weihenstephanensis* BPCOIN32, *Enterococcus faecalis* BP162, *Enterococcus faecalis* Lom1, *Enterococcus faecium* Nal, *Lactobacillus plantarum* BPE20, *Lactobacillus plantarum* BPE31, *Lactobacillus plantarum* BC79, *Lactobacillus plantarum* BC78, *Lactobacillus rhamnosus* BP2, *Lactobacillus rhamnosus* BP173, *Lactobacillus sanfranciscensis* M610, *Lactobacillus sanfranciscensis* M611, *Lactobacillus sanfranciscensis* M615, *Lactobacillus sanfranciscensis* M619, *Lactobacillus zeae* OR5, *Pediococcus pentosaceus* Prd1.

For producing the isolates, samples of biological sludge were taken from a water purifier in a biodiesel production plant. 45 mL of medium and 500 µL of sludge were added in tubes with a capacity of 50 mL.

Two different culture media with 15 g/L of glycerol were used as the carbon source: medium A (MA) and medium B (MB) richer in nutrients than medium A. Medium A (MA) has the following composition per liter: 30 g of glycerol, 0.75 g of KCl, 1.38 g of $NH_2PO_4.2H_2O$, 5.35 g of $(NH_4)_2SO_4$, 0.28 g of $Na_2SO_4$, 0.26 of $MgSO_4.7H_2O$, 0.42 g of citric acid, 2 g of yeast extract, 0.3 mL of a microelement solution (per liter: 34.2 g of $ZnCl_2$, 2.7 g of $FeCl_3.6H_2O$, 10 g of $MnCl_2.4H_2O$, 0.85 g of $CuCl_2.2H_2O$, 0.3 g of $H_3BO_3$, 23.8 g of $CoCl_2.6H_2O$). Medium B (MB) has the following composition per liter: 15-30 g of glycerol instead of glucose, 5.0 g of yeast extract, 5.0 g of tryptone, 7.0 g of $KH_2PO_4$, 7.0 g of $KH_2PO_4$, 1.0 g of $(NH_4)_2SO_4$, 0.25 g of $MgSO_4.7H_2O$, 0.12 g of $NaMoO_4.7H_2O$, 0.021 g of $CaCl_2.2H_2O$, 0.029 g of $CoCl_2.6H_2O$, 0.039 g of $Fe(NH_2)_2SO_4.6H_2O$, 2.0 mg of nicotinic acid, 0.172 mg of $Na_2SeO_3$, 0.02 mg of $NiCl_2$, and 10 mL of a microelement solution (per liter: 0.5 g of $Na_2EDTA$, 0.5 g of $MnCl_2.4H_2O$, 0.1 g of $H_3BO_3$, 1.0 mg of $CuCl_2.2H_2O$).

Two different temperatures were used for incubation: 30 and 37° C., and the cultures were incubated with and without stirring. After 48 hours they were transferred to a solid medium using culture media MA and MB solidified with 2% agar. The isolated colonies were inoculated in multiwell plates for massive screening with the same culture medium from which they came.

Qualitative methods for detecting and identifying the 2,3-butanediol producers used are described in the literature for identifying 2,3-butanediol (Desnuelle & Naudet, 1945)[3] and acetoin (Benjaminson et al. 1963[1]; Speckman & Collins, 1982)[8] once they are modified and adapted to the specific conditions of the present invention. The aforementioned microorganisms used in the screening were cultured for 16-18 hours in culture media with glycerol (media MA and MB) at 30° C., under stirring at 150 rpm.

The method followed for identifying acetoin in the medium is based on the fact that acetoin is oxidized by α-naphthol in the presence of air in basic medium. When the creatine and alkaline solution of α-naphthol are added to solutions with acetoin or diacetyl, a bright red complex having an indefinite chemical composition which can be measured in the spectrophotometer is formed. 120 µL of 0.5% creatine solution, 300 µL of 5% α-naphthol in ethanol, and 200 µL of 40% KOH solution are added to 1 mL of supernatant or untreated culture to identify the acetoin produced. The flow of the processed samples is increased in 96-well plates. For that purpose 100 µL of culture or supernatant, 12 µL of 0.5% creatine, 30 µL of a solution of 5% α-naphthol in ethanol, and 200 µL of 40% KOH solution were used. All the components must be mixed well by means of stirring in a vortex or pipetting. The red color appears after around 5-10 minutes and disappears about 30 minutes later.

The method followed for detecting 2,3-butanediol was based on oxidizing 2,3-butanediol to acetaldehyde and forming a blue complex with phenylhydrazine and sodium nitroprussiate which can be measured in the spectrophotometer. 4 mL of distilled water and 1 mL of 0.1 M $H_5IO_6$ were added to 1 mL of supernatant to identify the 2,3-butanediol produced, and the mixture is incubated for 30 minutes at room temperature. The reaction was neutralized with 2 drops (2×20 µL) of ethylene glycol. 1.5 mL of a saturated piperazine solution (30%) and 0.5 mL of 4% sodium nitroprussiate were added. The result was the appearance of a fleeting intense blue color in the presence of 2,3-butanediol. 150 µL of supernatant or 30 µL of supernatant with 120 µL of water were used in multiwell plates; 32 µL of $H_5IO_6$ were added and the mixture is incubated for 30 minutes at room temperature. 20 µL of ethylene glycol, 48 µL of the piperazine solution and 16 µL of the sodium nitroprussiate solution were added.

After incubating the selected microorganisms for 16-18 hours the colorimetric assays were conducted to select the colonies producing 2,3-butanediol and acetoin following the previously described methods. A total of 850 isolates were analyzed, and those that gave a positive result in the colorimetric tests (a total of 40 strains) were used to form a culture on a larger scale to verify the production of 2,3-butanediol.

Genomic DNA was obtained from the best producer strain, and it was identified at the genus and species level by sequencing zone 16S of the ribosomal repeat unit. Universal primers 616V, illustrated in SEQ. ID. NO. 1, and 630R, illustrated in SEQ. ID. NO. 2, were used for the PCR reaction. The PCR reaction mixture consisted of: 200 ng of genomic DNA, 5 µL of 10× buffer, 1.5 mM of $MgCl_2$, 1 U of Taq polymerase (Dinazyme), 200 µm of dNTPs, 1 µm of primers. The reaction conditions were: 1 cycle lasting 5 min at 94° C.; 35 cycles lasting 20 s at 94° C., 30 s at 56° C., 1 min at 72° C.; and 1 cycle lasting 10 min at 72° C.

The best producer strain was identified by comparing with databases (BlastN) as a strain belonging to bacterial species R. planticola, and specifically with wild-type strain CECT 843. The sequence of the 16S rDNA obtained with primer 616V is illustrated in SEQ. ID. NO. 3. This strain is classified in the Spanish Type Culture Collection (CECT) and German Type Culture Collection (DSMZ) as a risk type 1, i.e., it does not cause diseases in laboratory workers and animals.

b) Comparison of Activity of Wild-Type Strain R. planticola CECT 843 in Producing 2,3-butanediol from Glycerol with Other Microorganisms A fermentation assay was performed to compare 2,3-butanediol production capacity of the selected wild-type strain, R. planticola CECT843, with other microorganisms already described and known for their 2,3-butanediol production capacity. The microorganisms used in this comparative assay were: B. licheniformis D5M8785, Klebsiella oxytoca m5A1, P. polymyxa D5 356, P. polymyxa ATCC12321 and R. planticola IAM1133 mentioned in U.S. Pat. No. 5,254,467.

One of the media used in screening, i.e., the medium designated MB, was used with glycerol at 60 g/L. The assays were performed in 250 mL flasks with 50 mL of medium and incubating at 30° C., 100 rpm.

Culture growth was determined by means of measuring absorbance at 600 nm in spectrophotometer. The concentration of the substrate and of the metabolites produced was quantified by means of liquid chromatography in Waters 1525/2695 equipment with a differential refractive index detector and Rezex ROA Organic Acid column, with $H_2SO_4$ at 2.5 mM and a flow rate of 0.5 mL/min. Quantification was performed by means of comparison with standard curves of the products.

The results are shown in Table 1, which shows the percentage of glycerol consumed; $[BD]_{max}$ is the maximum concentration of 2,3-butanediol attained; η indicates the conversion yield in percentage, in grams of 2,3-BD produced with respect to grams of glycerol consumed; $[Acetoin]_{max}$ is the maximum concentration of acetoin produced in g/L; $[PD]_{max}$ is the maximum concentration of 1,3-propanediol; OD refers to the maximum optical density at 600 nm measured in culture; n.d.: not detected.

TABLE 1

Comparison of 2,3-butanediol producer strains.

| Strain | Glycerol consumed | $[BD]_{max}$ | $[Acetoin]_{max}$ | $[PD]_{max}$ | η | $OD_{max}$ |
|---|---|---|---|---|---|---|
| B. licheniformis D5M8785 | 27.5 | 1.26 | 3.6 | n.d. | 7.8% | 11.43 |
| Klebsiella oxytoca m5A1 | 98.0 | 15.3 | 10.8 | 1.6 | 26.6% | 21.16 |
| P. Polymyxa ATCC12321 | 55.0 | 4.6 | 7.2 | n.d. | 14.2% | 20.81 |
| P. Polymyxa D5M356 | 35.5 | 4.7 | 3.4 | n.d. | 22.6% | 14.50 |
| R. Planticola IAM1133 | 16.2 | 2.9 | 2.3 | n.d. | 30.0% | 9.3 |
| R. Planticola CECT 843 | 99.5 | 23.2 | 2.3 | n.d. | 40.0% | 21.63 |

It is observed in this table that the best 2,3-BD producers are wild-type R. planticola and K. oxytoca m5a1. They both consume virtually the entire starting substrate, but R. planticola CECT843 has a higher yield, producing 23.3 g/L of 2,3-BD.

The enormous difference observed between the two R. planticola strains should be mentioned. R. planticola strain IAM133 consumes only 16% of total glycerol and generates only 2.9 g/L of 2,3-BD compared to 23.2 g/L produced by R. planticola CECT843. For this reason, R. planticola strain CECT 843 is far better in terms of production and yield than strain R. planticola IAM1133.

c) Characterization of the Tolerance to Glycerol and 2,3-butanediol

In addition to selecting a species with a high capacity to convert glycerol into 2,3-butanediol, the capacity of the microorganism's growth and viability not being affected by high concentrations of glycerol added to the medium for the conversion process, as well as the high concentrations of conversion product, 2,3-butanediol, generated during the process must also be taken into account.

Therefore, in order to determine tolerance of the selected strain to the substrate and to the product obtained after fermentation, growth assays were performed at increasing concentrations of both compounds in the culture medium designated medium MA. Klebsiella oxytoca strain m5a1 was chosen as the control strain for comparison purposes as it was the second best 2,3-butanediol producer under the previously examined conditions. Furthermore, this strain is one of the most widely studied and used in fermentations with glycerol for producing 1,3-propanediol and 2,3-butanediol.

The following concentrations of glycerol were assayed: 15, 20, 25, 30, 35, 40, 50, 60, 70 and 80 g/L. The concentrations of 2,3-butanediol assayed were: 15, 20, 25, 30, 35, 40, 50, 60, 70 and 80 g/L. In both cases, glucose was used as growth control as a carbon source at 15 g/L. The assays were performed by means of incubating in Multiskan Ascent incubation equipment (Thermo Electron Corporation) at 30° C. Culture growth was monitored by means of measuring absorbance or optical density ($OD_{600}$) for 24 hours.

Figure 2:
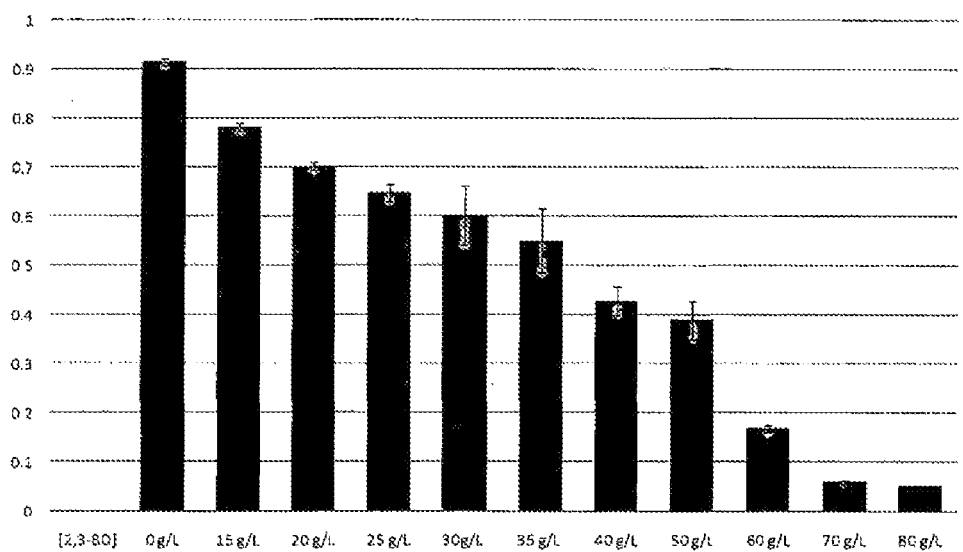
FIG. 2A shows growth of *R. planticola* strain CECT843 in increasing concentrations of 2,3-butanediol. The average results of four replicas are illustrated.
FIG. 2B shows growth of *K. oxytoca* strain m5a1 in increasing concentrations of 2,3-butanediol. The average results of four replicas are illustrated.
Figure 2:
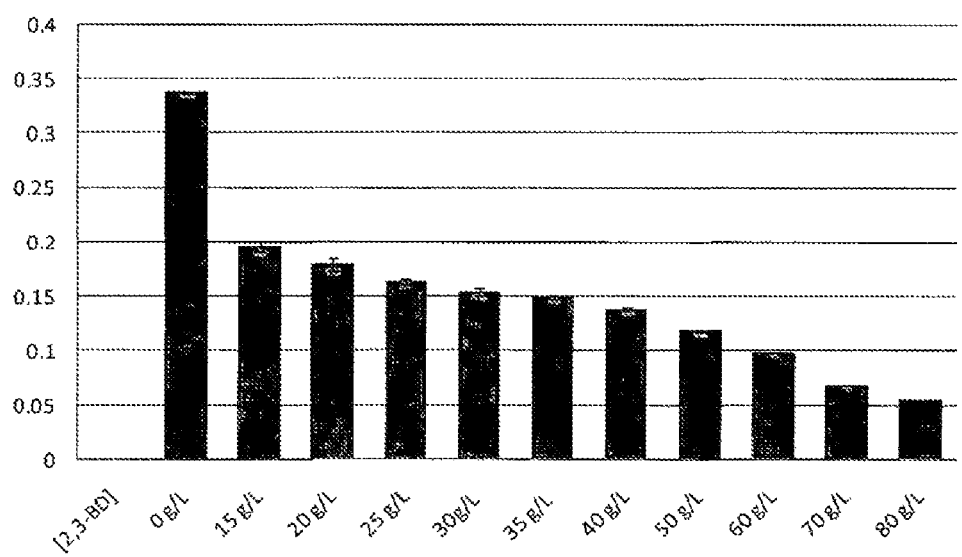

FIG. 1 shows the results of growth with glycerol and FIG. 2 shows the $OD_{600}$ attained with 2,3-butanediol. *R. planticola* strain CECT843, selected as the best producer, furthermore tolerates both compounds better than the control *K. oxytoca* strain m5a1 does. *R. planticola* strain CECT843 maintains the same level of growth up to concentrations of 60 g/L of glycerol, whereas growth of *K. oxytoca* starts to be inhibited after 40 g/L. With respect to the presence of 2,3-butanediol, growth of *K. oxytoca* drops to 50% with 15 g/L of the compound, whereas this effect does not occur in *R. planticola* strain CECT843 until reaching concentrations of 35 g/L of 2,3-butanediol.

Therefore, the selection of *R. planticola* wild-type strain also proved to be the right choice in terms of industrial viability due to its high tolerance to glycerol and 2,3-butanediol.

d) Producing *R. planticola* Strains CECT8158 and CECT8159 from the Wild-Type Strain A strategy of randomly induced mutagenesis both with a chemical mutagen (ethyl methanesulfonate, EMS) and by exposure to UV radiation, followed by growth in bromate/bromide plates, was followed for producing 2,3-butanediol super-producer strains from previously selected wild-type strain CECT843.

This method allows selecting mutants with less acid secretion. Since the production of organic acids competes with the production pathway of 2,3-BD, a lower production of acids must give rise to an increase in the production of 2,3-BD.

Figure 3:
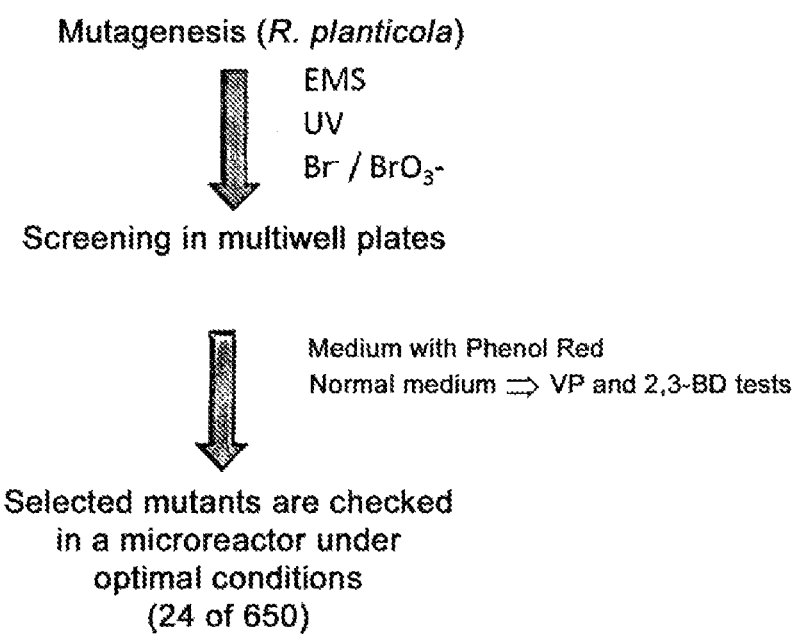
FIG. 3 shows a diagram of the method of random mutagenesis for producing and selecting *R. planticola* strains CECT8158 and CECT8159.

FIG. 3 shows a diagram of the method.

Around $2\times10^8$ cells/mL of a culture obtained in exponential phase in a culture medium with 30 g/L of glycerol (medium MB) were used for mutagenesis with EMS. The cells were washed with 0.1 M phosphate buffer pH 7.0 and resuspended in the same volume of the buffer. The cell suspension was distributed into aliquots of 1 mL in Eppendorf tubes. Different amounts of EMS (0, 2, 4, 6, 8, 10, 20 μL per mL of culture) were added and they were incubated for 1 hour at 30° C. The tubes were centrifuged and two washes were performed with phosphate buffer. The mutagen was neutralized with two washes with sodium thiosulfate, and the content of each tube was resuspended in 5 mL of culture medium with 30 g/L of glycerol. It was all incubated at 30° C. for 16-18 hours for recovery. Counts were taken in LB medium to determine the percentage of death. The dose chosen for mutagenesis was 10 μL/mL as it provides 95% of death.

The cells were subsequently seeded in selection plates with bromide/bromate (100 mM of NaBr, and 100 mM of $NaBrO_3$, 12 g/L of glucose, 4 g/L of peptone, 1.2 g of meat extract, 2 g/L of NaCl, and 16 g/L of agar) and were incubated 2-3 days until colonies were formed. Different proportions of salts and different values of pH were tested to determine the optimal concentration of bromide/bromate that allowed obtaining isolated colonies: 160 mM/40 mM, 130 mM/32.5 mM, 100 mM/25 mM and 100 mM/100 mM $Br^-/BrO_3^-$, and pH 7.0, 6.5 and 6.0. The 100 mM/100 mM combination of both salts and pH 6.0 was a determining condition for selecting strains that are altered in metabolism of acids (proton suicide method, Cueto & Méndez, 1990).

For mutagenesis by exposure to UV radiation, 1 mL of a washed cell suspension in phosphate buffer ($2\times10^8$), which cells are from a culture in exponential growth phase, was seeded directly in plates containing 100 mM $Br^-/BrO_3^-$ pH 6.0. Serial dilutions of the cultures were seeded in plates containing LB medium as a control to analyze the follow-up of the effect of radiation on cell viability. The plates were subjected to different UV light exposure times: 0, 15, 30, 45 and 60 seconds. The plates were incubated in the dark until colonies were formed. A 45-second exposure time was selected as the most suitable radiation time as it provides a percentage of death of 95%.

The colonies obtained from the of $Br^-/BrO_3^-$ plates were assayed in multiwell plates in fermentation medium with 30 g/L glycerol (Nakashimada et al., 1998), supplemented with phenol red at a concentration of 0.008%. This coloring turns yellow under pH 6.4, which allowed discarding mutants that reduced pH below this figure and thereby selecting those mutants that produce less acid. The previously described colorimetric assays were performed for detecting acetoin and 2,3-butanediol.

650 mutants were thereby analyzed, from which 650 mutants a first selection was made comprising mutants that produced less acid in multiwell plate assays and gave a positive result in the colorimetric tests for detecting 2,3-BD and acetoin, resulting in a total of 24 strains.

These 24 strains were assayed in a microreactor under the optimal growth and production conditions determined for wild-type strain CECT 843. The consumption of glycerol and the concentration of 2,3-butanediol produced during the assay were analyzed. Growth was measured by means of absorbance at 600 nm in a spectrophotometer. Table 2 shows the results of the assays, comparing the different selected mutants with the wild-type strain. Said table shows maximum concentration of 2,3-BD, acetoin and ethanol in g/L; the glycerol consumed in g/L, and the yield in g 2,3-butanediol/g glycerol consumed.

Cultures were done in medium MB with 60 g/L of glycerol and an initial pH of 6.8. Temperature (33° C.) and oxygenation were controlled, establishing 5% DO (dissolved oxygen) as a reference point. Samples were periodically taken to analyze the content of the supernatant and bacterial growth. The maximum for 2,3-butanediol was attained at about 30 hours.

TABLE 2

Comparison of mutant strains with the wild-type strain.

|  | $[BD]_{max}$ | $[Glycerol]_{cons}$ | η g/g | $[Acetoin]_{max}$ | $[EtOH]_{max}$ |
|---|---|---|---|---|---|
| CECT843 843Wild | 20.4 ± 2.1 | 47.2 ± 2.9 | 0.43 ± 0.2 | 1.5 ± 0.4 | 0.4 ± 0.2 |
| A1 | 18.0 ± 8.7 | 38.9 ± 11.9 | 0.45± | 0.9± | 0.8 ± 0.5 |
| A2 | 9.4 ± 2.2 | 22.5 ± 5.7 | 0.42± | 1.6± | 0.4 ± 0.1 |
| A3 | 17.8 ± 2.9 | 35.3 ± 6.3 | 0.51± | 0.9 ± 0.4 | 0.5 ± 0.0 |
| A7 | 27.8± | 40.6 ± 2.7 | 0.67± | 2.0 ± 1.6 | 0.3 ± 0.4 |
| C3 | 12.2± | 27.4 ± 4.1 | 0.45± | 0.9 ± 0.2 | 0.5 ± 0.1 |
| E1 | 4.2 ± 2.2 | 14.1 ± 6.2 | 0.29± | 1.5 ± 0.4 | 0.2 ± 0.0 |
| E12 | 3.9 ± 1.0 | 15.9 ± 1.8 | 0.24± | 1.3 ± 0.4 | 0.3 ± 0.1 |

TABLE 2-continued

Comparison of mutant strains with the wild-type strain.

| | [BD]$_{max}$ | [Glycerol]$_{cons}$ | η g/g | [Acetoin]$_{max}$ | [EtOH]$_{max}$ |
|---|---|---|---|---|---|
| F6 | 11.1± | 29.8 ± 2.8 | 0.38± | 0.8 ± 0.2 | 0.2 ± 0.0 |
| F11 | 9.8 ± 1.1 | 28.2 ± 2.8 | 0.35± | 0.7 ± 0.2 | 0.3 ± 0.1 |
| H7 | 21.3± | 42.5 ± 9.9 | 0.51± | 1.3 ± 0.6 | 1.0 ± 0.5 |
| H10 | 19.4± | 40.6 ± 0.1 | 0.48± | 1.1 ± 0.2 | 0.4 ± 0.0 |
| IA1 | 20.7± | 45.1 ± 2.5 | 0.46± | 1.2 ± 0.0 | 0.6 ± 0.0 |
| IA11 | 2.3 ± 0.2 | 13.7 ± 1.0 | 0.17± | 1.3 ± 0.1 | 0.2 ± 0.0 |
| IA12 | 20.4 ± 1.6 | 44.1 ± 0.3 | 0.46± | 1.4 ± 0.8 | 0.4 ± 0.0 |
| IB12 | 10.9 ± 3.6 | 30.2 ± 5.6 | 0.37± | 1.3 ± 1.1 | 0.4 ± 0.0 |
| IH1 | 17.0 ± 5.8 | 45.1 ± 4.1 | 0.37± | 1.9 ± 0.9 | 0.3 ± 0.0 |
| IIA12 | 19.4 ± 8.3 | 41.3 ± 4.1 | 0.46± | 1.0 ± 0.4 | 0.5 ± 0.0 |
| IIB2 | 11.9 ± 1.1 | 37.2 ± 2.7 | 0.32 ± 0.5 | 0.7 ± 0.0 | 0.3 ± 0.0 |
| IIB12 | 19.2 ± 0.9 | 45.3 ± 0.7 | 0.42± | 1.9 ± 1.0 | 0.5 ± 0.0 |
| IC12 | 21.4 ± 6.4 | 45.5 ± 3.8 | 0.47± | 2.2 ± 1.2 | 0.3 ± 0.0 |
| IIIA1 | 21.3 | 45.1 | 0.51 | 1.4 | 0.5 |
| 111A3 | 21.8 | 44.3 | 0.49 | 2.1 | 0.3 |
| 111A5 | 12.0 | 28.0 | 0.43 | 0.8 | 0.4 |
| IIIC9 | 11.7 | 37.4 | 0.31 | 0.7 | 0.2 |

[BD]$_{max}$ is the maximum concentration of 2,3-butanediol attained;
[Glycerol]$_{cons}$ is the concentration of glycerol consumed;
η indicates the conversion yield in grams of 2,3-BD produced with respect to grams of glycerol consumed;
[Acetoin]$_{max}$ is the maximum concentration of acetoin produced, measured in g/L; and
[EtOH]$_{max}$ is the maximum concentration of ethanol produced, measured in g/L.

After this second evaluation the 7 strains A7, H7, IA1, IA12, IIC12, IIIA1 and IIIA3 were selected considering criteria consisting of a higher concentration of 2,3-BD and higher yield than the wild-type strain. Mutants IA1, IA12, IIC12, IIIA1 and IIIA3 were obtained by mutagenesis with EMS. Mutant H7 resulted from spontaneous mutagenesis of the wild-type strain seeded in plates with 100 mM NaBr/NaBrO$_3$. Mutant A7 was produced by exposure to UV radiation.

e) Selection of *Raoultella Planticola* Strains IA1 (CECT8158) and IIIA3 (CECT8159) as the Best 2,3-butanediol Producer Strains The assays described above were performed again to compare the 2,3-butanediol production capacity of the 7 mutants selected in the preceding step in microfermentation equipment, using wild-type strain CECT 843 as a control under the same conditions described in the preceding section Cultures were done in medium MB with 60 g/L of glycerol.

The general conclusions of the results of the assay performed are illustrated in Table 4. Lower production of acetoin and biomass is observed in the mutants with respect to the wild-type strain, which would explain the higher 2,3-butanediol conversion yield in mutated strains.

Figure 4:
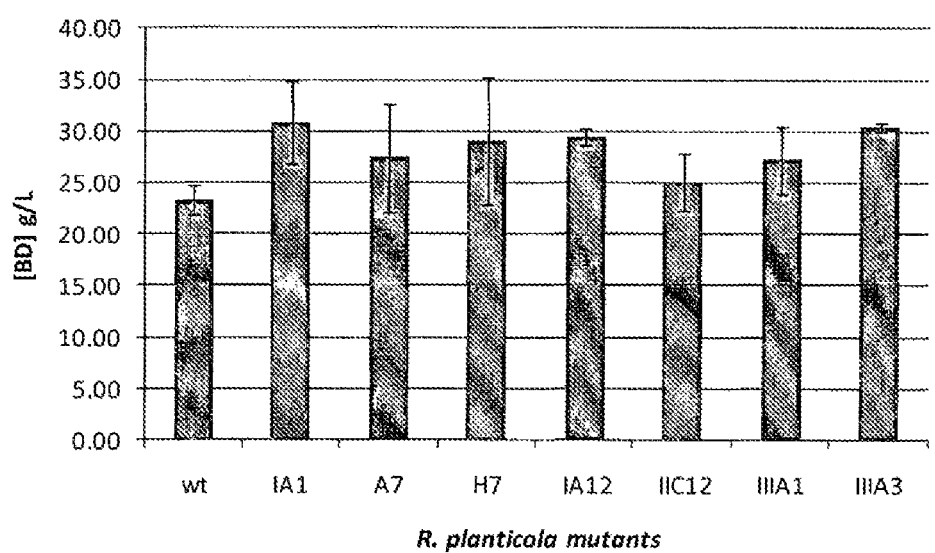
FIG. 4 shows production of 2,3-butanediol from different strains of species *R. planticola*.

The results of the assay performed are provided in the following table:

Additionally, FIG. 4 shows how the concentration of 2,3-butanediol attained for strain IA1 and strain IIIA3, both obtained by EMS-induced random mutagenesis, and subsequent selection in bromate/bromide plates according to the present invention, are better than the rest of the tested strains.

Specifically, mutants IA1 and IIIA3 generated concentrations of 2,3-butanediol around 30 g/L and yields around 50%. The rest of the strains assayed produced around 30% more 2,3-butanediol than the wild-type strain did.

In conclusion, mutant strains of *R. planticola* CECT843 obtained by EMS-induced random mutagenesis and subsequent selection in bromate/bromide plates can be used in the industrial production of 2,3-butanediol from glycerol. Preferably, mutant strains IA1 (CECT8158) and IIIA3 (CECT8159) are shown to have greater industrial viability for the purpose of the present invention.

II. Selecting Optimal Conditions of the Fermentation Process for Producing 2,3-butanediol The effect of variables such as temperature (T), initial concentration of glycerol ([Gly]) and initial concentration of cobalt ([$Co^{2+}$]), consumption of the carbon source (glycerol) and biomass growth in the process of conversion into 2,3-butanediol was analyzed to identify the optimal conditions for the conversion of glycerol into 2,3-butanediol using the *R. planticola* strains of the present invention. A factorial experiment design was used for that purpose.

TABLE 4

Comparative assays of wild-type *R. planticola* and mutants.

| | [BD]$_{max}$ | [Glycerol]$_{cons}$ | η (g/g) | [Acetoin]$_{max}$ | [EtOH]$_{max}$ |
|---|---|---|---|---|---|
| CECT843 | 23.3 ± 1.4 | 64.7 ± 0.0 | 0.36 ± 0.02 | 6.7 ± 0.2 | 0.6 ± 0.3 |
| IA1 | 30.8 ± 3.9 | 62.5 ± 0.9 | 0.49 ± 0.07 | 5.0 ± 1.0 | 0.5 ± 0.0 |
| A7 | 27.4 ± 5.2 | 60.5 ± 7.3 | 0.45 ± 0.06 | 3.4 ± 1.4 | 0.2 ± 0.1 |
| H7 | 25.3 ± 7.8 | 55.2 ± 7.3 | 0.45 ± 0.01 | 3.6 ± 1.7 | 0.4 ± 0.0 |
| IA12 | 29.4 ± 0.8 | 63.2 ± 0.7 | 0.47 ± 0.00 | 5.0 ± 0.7 | 0.3 ± 0.0 |
| IIC12 | 25.1 ± 2.7 | 56.0 ± 7.1 | 0.45 ± 0.10 | 2.0 ± 1.0 | 0.7 ± 0.4 |
| IIIA1 | 37.1 ± 3.3 | 60.9 ± 0.9 | 0.46 ± 0.07 | 1.9 ± 0.2 | 0.9 ± 0.4 |
| IIIA3 | 30.5 ± 0.4 | 57.6 ± 5.5 | 0.50 ± 0.00 | 2.4 ± 1.5 | 0.8 ± 0.0 |

As an objective of the factorial design, actual yield ($Y_1$), calculated as shown in equation [1], consumption of glycerol ($Y_2$), defined in equation [2], and optical density, given that it is proportional to the amount of biomass ($Y_3$), were defined as functions to be maximized.

$$\eta = \frac{[2,3-BD]}{[Gly]_{INITIAL}} \quad [1]$$

$$[Gly]_{consumed} = \frac{[Gly]_{INITIAL} - [Gly]_{FINAL}}{[Gly]_{INITIAL}} \quad [2]$$

The assays were performed in a microreactor, in the fermentation culture medium designated medium MB (Nakashimada et al., 1998), with the required changes in the concentration of glycerol (concentration of glycerol of 60, 75 and 90 g/L) and cobalt salt (0.012, 0.024 and 0.036 g/L of $CoCl_2$) and under the conditions indicated in Table 5. The amount of dissolved oxygen was established at 5%. 3 mL were used as the culture volume.

TABLE 5

Experiment design.

| Experiment | A T (° C.) | B % $O_2$ | C [Glycerol] g/L | D [$COCl_2$] g/L | A T (° C.) | B [Glycerol] g/L | C [$COCl_2$] g/L |
|---|---|---|---|---|---|---|---|
| E1 | 28 | 5 | 75 | 0.035 | 1 | 2 | 3 |
| E2 | 30 | 5 | 60 | 0.012 | 2 | 1 | 1 |
| E3 | 33 | 5 | 90 | 0.024 | 3 | 3 | 2 |
| E4 | 28 | 5 | 90 | 0.012 | 1 | 3 | 1 |
| E5 | 30 | 5 | 75 | 0.024 | 2 | 2 | 2 |
| E6 | 33 | 5 | 60 | 0.036 | 3 | 1 | 3 |
| E7 | 28 | 5 | 60 | 0.024 | 1 | 1 | 2 |
| E8 | 30 | 5 | 90 | 0.036 | 2 | 3 | 3 |
| E9 | 33 | 5 | 75 | 0.012 | 3 | 2 | 1 |

Table 6 shows the results obtained in each of the experiments considered in Table 5. By means of statistical analysis of the variability associated with each factor, it was determined that the concentration of glycerol, temperature and concentration of cobalt salts had a significant effect on the target functions.

TABLE 6

Experimental results.

| Experiment | $[BD]_{max}$ | $Y_1$ η (g/g) | $Y_2$ [Glycerol]$_{cons}$ | $Y_3$ OD |
|---|---|---|---|---|
| E1 | 18.00 | 0.240 | 37.97 | 18.00 |
| E2 | 14.21 | 0.237 | 34.58 | 19.49 |
| E3 | 20.36 | 0.226 | 23.25 | 11.25 |
| E4 | 15.21 | 0.169 | 27.00 | 23.03 |
| E5 | 19.04 | 0.254 | 40.00 | 25.20 |
| E6 | 22.30 | 0.372 | 54.37 | 31.72 |
| E7 | 15.54 | 0.259 | 33.94 | 17.96 |
| E8 | 18.02 | 0.200 | 26.55 | 24.65 |
| E9 | 14.02 | 0.187 | 32.26 | 25.06 |

The optimal levels for each factor are shown in Table 7.

TABLE 7

Optimal levels of each factor.

| Variable | $Y_1$ | $Y_2$ | $Y_3$ |
|---|---|---|---|
| T (° C.) | 33 | 33 | 30 |
| [Glyc.] (g/L) | 60 | 60 | 75 |
| [Co] (g/L) | 0.036 | 0.036 | 0.024 |

Based on the analysis of the results obtained in this section, it was also concluded that the viable and optimal fermentation reaction conditions of the method for producing 2,3-butanediol are the following:

Reaction temperature: between 28 and 37° C., preferably, 33° C.

Presence of cobalt salts, such as $CoCl_2$ for example: between 0.012 and 0.050 g/L, preferably 0.036 g/L.

Presence of glycerol in the culture medium: between 10 and 90 g/L, preferably 60 g/L.

pH between 7.5 and 5.5, preferably 6.8 and uncontrolled during fermentation.

Other carbon sources can be added to the culture medium in addition to glycerol, such as yeast extract rich in vitamins and amino acids, for example, in amounts between 0.5-8 and, preferably 5 g/L.

The culture medium may also contain other inorganic nitrogen sources, such as, ammonium sulfate, for example, or complex organic nitrogen sources, such as yeast extract, peptone, tryptone, corn steep liquor, urea or glutamate.

As regards reaction time, said time is estimated between 12 and 48 hours, preferably, 30 hours.

The concentration of dissolved oxygen in the medium with respect to the concentration of saturation is estimated around 0%-20%, preferably 5%.

The fermentation process of the present invention can be carried out discontinuously in fed-batch or batch mode with both free and immobilized cells, in Applikon bioreactors, Braun Biotech bioreactors or in bioreactors having similar characteristics, having a capacity of 1 to 5 liters and greater, in which stirring between 200 and 700, preferably 500 rpm, is determined to be suitable for the purpose of the present invention.

III. Separating the 2,3-butanediol Product Obtained in Fermentation

As previously discussed, 2,3-butanediol formed in the fermentation process using novel strains of *R. planticola* strains CECT8158 and CECT8159 of the present invention, is separated from the culture supernatant by frequently used methods.

When separating 2,3-butanediol from the culture broth, separation of the biomass and other solids from the fermentation broth can be carried out by means of filtration or centrifugation. Various techniques can be used for subsequent purification of 2,3-butanediol, such as steam stripping, countercurrent steam stripping, solvent extraction, reactive extraction, repulsive extraction, reverse osmosis and pervaporation (Xiu & Zeng, 2008).

Solvents such as ethyl acetate, tributylphosphate, diethyl ether, n-butanol, dodecanol and oleyl alcohol can be used in liquid-liquid extraction. As a prior step, water must be removed by means of evaporation and by means of microfiltration and reverse osmosis. PEG/dextran systems can be used for two-phase aqueous extraction.

Repulsive extraction, or precipitation by crystallization, requires previously removing water from the reaction broth. Extraction of 2,3-BD has been achieved using KCl or $K_2CO_3$ In reactive extraction, 2,3-BD can react with formaldehyde to produce a methyl acetal under acid catalysis. The methyl acetal of 2,3-butanediol is pooled as an oil in the upper phase and to recover it, it is reacted with methanol to form 2,3-BD and methylal. Methylal, or dimethoxymethane, is in turn hydrolyzed to methanol and formaldehyde.

Pervaporation, or vacuum membrane distillation, concentrates large amounts of the compound by using microporous polytetrafluoroethylene (PTFE) membranes.

Example 1

Producing 2,3-butanediol from Glycerol Using Wild-Type *R. planticola*: Selecting Optimal Operating Conditions with a Simple Culture Medium Optimal operating conditions were determined with a simple culture medium (medium C, MC) suitable for working at higher fermentation scales for producing 2,3-butanediol using *R. planticola* wild-type strain CECT843 from pure glycerol as a carbon source.

Medium MC has the following composition per liter: 2 g of $NH_4Cl$, 6 g of $KH_2PO_4$, 12 g of $Na_2HPO_4$, 1 g of NaCl, 246 mg of $MgSO_4.7H_2O$, 14.7 g of 14.7 g/L $CaCl_2$-$2H_2O$.

An experiment design contemplating the following factors was implemented:
  Temperature: the interval studied was 26 to 35° C.
  Type of culture medium: assays were performed in two synthetic media, medium A and medium C.
  Concentration of yeast extract: the interval studied was 0.5 to 1.5 g/L
  Addition of citric and/or acetic acid: the effect of the addition of either organic acid at a concentration of 0.42 g/L or the mixture of both (at a concentration of 0.21 g/L) was observed, comparing it with the result obtained in a control experiment.

Experiments were conducted in batch mode, in 50 mL bottles with 10 mL of the corresponding culture medium. The initial concentration of glycerol was 30 g/L. Stirring was set at 175 rpm in all the experiments. Initial pH of the medium was 7, and it developed freely throughout fermentation, dropping to values close to 5.

Based on the analysis of the results obtained in the experimental design, it was determined that the conditions that optimize producing 2,3-butanediol for each factor in the assayed culture medium are the following:
  Temperature 28° C.
  Medium C
  Concentration of yeast extract: 1.5 g/L
  Addition of 0.42 g/L of citric acid.

The results obtained for the optimal conditions are shown in Table 8, which illustrates the values obtained for the glycerol consumed in g/L, [glycerol]$_{cons}$; concentration of 2,3-butanediol produced, [BD]$_{max}$; maximum concentration of acetoin produced, [acetoin]$_{max}$; η is the yield in g/g; maximum concentration of ethanol produced, [EtOH]$_{max}$.

TABLE 8

Producing 2,3-butanediol using *R. planticola* strain CECT843 with pure glycerol.

| [BD]$_{max}$ | [Glycerol]$_{cons}$ | η (g/g) | [Acetoin]$_{max}$ | [EtOH]$_{max}$ |
|---|---|---|---|---|
| 8.1 | 29.5 | 0.28 | 3.3 | 1.2 |

Culture growth was determined by means of measuring absorbance at 600 nm in a spectrophotometer. The concentration of substrate and metabolites produced was quantified by means of high performance liquid chromatography in Agilent Technologies 1100 series equipment with a diode array detector (measurement taken at 276 nm) and a refractive index detector. The column used was a Rezex ROA Organic Acid column. The mobile phase used was a diluted sulfuric acid solution (acid concentration of 0.005 N), the flow rate of which was set at 0.5 mL/min. Compounds were quantified by means of comparison with standard curves of the products.

Example 2

Producing 2,3-butanediol from Glycerol Using *R. planticola* CECT8158 (Mutant IA1) in Medium MC.

An experiment was conducted in batch mode at the orbital incubator level in 50 mL bottles with 10 mL of culture medium to evaluate the 2,3-butanediol production capacity of *R. planticola* mutant strain CECT8158 in synthetic medium MC.

The conditions optimized for wild-type strain CECT843 and modified synthetic medium MC, with an initial concentration of pure glycerol of 60 g/L, were used. The fermentation conditions were set at: temperature 28° C.; stirring 175 rpm. Initial pH of the medium was 7, and it developed freely throughout fermentation, dropping to values close to 5.

The results are shown in Table 9, which illustrates the values obtained for the glycerol consumed in g/L, [glycerol]$_{cons}$; concentration of 2,3-butanediol produced, [BD]$_{max}$; maximum concentration of acetoin produced, [acetoin]$_{max}$; η is the yield in g/g; maximum concentration of ethanol produced, [EtOH]$_{max}$.

TABLE 9

Producing 2,3-butanediol using *R. planticola* mutant strain IA1 in medium MC.

| [BD]$_{max}$ | [Glycerol]$_{cons}$ | η (g/g) | [Acetoin]$_{max}$ | [EtOH]$_{max}$ |
|---|---|---|---|---|
| 23.4 | 61.5 | 0.38 | 3.7 | 1.9 |

Culture growth was determined by means of measuring absorbance at 600 nm in a spectrophotometer. The concentration of substrate and metabolites produced was quantified by means of high performance liquid chromatography in Agilent Technologies 1100 series equipment with a diode array detector (measurement taken at 276 nm) and a refractive index detector. The column used was a Rezex ROA Organic Acid column. The mobile phase used was a diluted sulfuric acid solution (concentration of the acid 0.005 N), the flow rate of which was maintained at 0.5 mL/min. Compounds were quantified by means of comparison with standard curves of the products.

Example 3

Producing 2,3-butanediol from Glycerol Using *R. planticola* CECT8159 (IIIA3) in Medium MC An experiment was conducted in batch mode in 50 mL bottles with 10 mL of culture medium to evaluate the 2,3-butanediol production capacity of *R. planticola* mutant strain IIIA3 in synthetic medium.

The conditions optimized for the wild-type strain and modified synthetic medium MC, with an initial concentration of pure glycerol of 60 g/L, were used. The fermentation conditions were set at: temperature 28° C.; stirring 175 rpm. Initial pH of the medium was 7, and it developed freely throughout fermentation, dropping to values close to 5.

The results are shown in Table 10, which illustrates the values obtained for the glycerol consumed in g/L, [glycerol]$_{cons}$; concentration of 2,3-butanediol produced, [BD]$_{max}$; maximum concentration of acetoin produced, [acetoin]$_{max}$; η is yield in g/g; maximum concentration of ethanol produced, [EtOH]$_{max}$.

TABLE 10

Producing 2,3-butanediol using R. planticola strain CECT8159 in medium MC

| [BD]$_{max}$ | [Glycerol]$_{cons}$ | η (g/g) | [Acetoin]$_{max}$ | [EtOH]$_{max}$ |
|---|---|---|---|---|
| 18.5 | 60.8 | 0.30 | 3.8 | 1.2 |

Culture growth was determined by means of measuring absorbance at 600 nm in a spectrophotometer. The concentration of substrate and metabolites produced was quantified by means of high performance liquid chromatography in Agilent Technologies 1100 series equipment with a diode array detector (measurement taken at 276 nm) and a refractive index detector. The column used is Rezex ROA Organic Acid. The mobile phase used is a diluted sulfuric acid solution (concentration of the acid 0.005 N), the flow rate of which is 0.5 mL/min. Compounds were quantified by means of comparison with standard curves of the products.

Example 4

Producing 2,3-butanediol from Glycerol Using R. planticola Wild-Type Strain CECT 843 in a 1-Liter Scale Bioreactor An assay was performed in batch mode in an Applikon fermenter having a 1-liter fermentation volume with wild-type strain CECT 843. The conditions described as optimal for medium MB with glycerol at an initial concentration of 60 g/L were used. The fermentation conditions were set at 33° C., 500 rpm and 5% dissolved oxygen. Initial pH of the medium was 6.8, and it was not controlled during the experiment so that pH drops slightly.

The results are shown in Table 11, which illustrates the values obtained for the glycerol consumed in g/L, [glycerol]$_{cons}$; concentration of 2,3-butanediol produced, [BD]$_{max}$; maximum concentration of acetoin produced, [acetoin]$_{max}$; η is the yield in g/g; maximum concentration of ethanol produced, [EtOH]$_{max}$.

TABLE 11

Producing 2,3-butanediol using wild-type strain CECT 843 in a 1-liter fermenter.

| [BD]$_{max}$ | [Glycerol]$_{cons}$ | η (g/g) | [Acetoin]$_{max}$ | [EtOH]$_{max}$ |
|---|---|---|---|---|
| 22.0 | 64.2 | 0.34 | 6.8 | 0.9 |

Culture growth was determined by means of measuring absorbance at 600 nm in a spectrophotometer. The concentration of substrate and metabolites produced was quantified by means of liquid chromatography in Waters 1525/2695 equipment with a differential refractive index detector and Rezex ROA Organic Acid column, with 2.5 mM H$_2$SO$_4$ and a flow rate of 0.5 mL/min. Quantification was performed by means of comparison with standard curves of the products.

Example 5

Producing 2,3-butanediol from Glycerol Using R. planticola Strain CECT8158 (Mutant IA1) in a 1-Liter Scale Bioreactor An assay was performed in batch mode in an Applikon fermenter having a 1-liter fermentation volume with the mutant strain IA1. The conditions described as optimal for the wild-type strain and medium MB with glycerol at an initial concentration of 60 g/L were used. The fermentation conditions were set at 33° C., 500 rpm and 5% dissolved oxygen. Initial pH of the medium was 6.8, and it was not controlled during the experiment so that pH drops slightly.

The results are shown in Table 12, which illustrates the values obtained for the glycerol consumed in g/L, [glycerol]$_{cons}$; concentration of 2,3-butanediol produced, [BD]$_{max}$; maximum concentration of acetoin produced, [acetoin]$_{max}$; η is the yield in g/g; maximum concentration of ethanol produced, [EtOH]$_{max}$.

TABLE 12

Producing 2,3-butanediol using strain IA1 in a 1-liter fermenter.

| [BD]$_{max}$ | [Glycerol]$_{cons}$ | η (g/g) | [Acetoin]$_{max}$ | [EtOH]$_{max}$ |
|---|---|---|---|---|
| 33.6 | 61.8 | 0.54 | 4.3 | 0.5 |

Culture growth was determined by means of measuring absorbance at 600 nm in a spectrophotometer. The concentration of substrate and metabolites produced was quantified by means of liquid chromatography in Waters 1525/2695 equipment with a differential refractive index detector and Rezex ROA Organic Acid column, with 2.5 mM H$_2$SO$_4$ and a flow rate of 0.5 mL/min. Quantification was performed by means of comparison with standard curves of the products.

Example 6

Producing 2,3-butanediol from Glycerol Using R. planticola Strain CECT8159 (Mutant IIIA3) in a 1-Liter Scale Bioreactor An assay was performed in batch mode in an Applikon fermenter having a 1-liter fermentation volume with mutant strain IIIA3. The conditions described as optimal for wild-type strain CECT843 and medium MB with glycerol at an initial concentration of 60 g/L were used. The fermentation conditions were set at 33° C., 500 rpm and 5% dissolved oxygen. Initial pH of the medium was 6.8, and it was not controlled during the experiment so that pH drops slightly.

The results are shown in Table 13, which illustrates the values obtained for the glycerol consumed in g/L, [glycerol]$_{cons}$; concentration of 2,3-butanediol produced, [BD]$_{max}$; maximum concentration of acetoin produced, [acetoin]$_{max}$; η is the yield in g/g; maximum concentration of ethanol produced, [EtOH]$_{max}$.

TABLE 12

Producing 2,3-butanediol using strain IIIA3 in a 1-liter fermenter.

| [BD]$_{max}$ | [Glycerol]$_{cons}$ | η (g/g) | [Acetoin]$_{max}$ | [EtOH]$_{max}$ |
|---|---|---|---|---|
| 30.7 | 61.3 | 0.50 | 3.5 | 0.8 |

Culture growth was determined by means of measuring absorbance at 600 nm in a spectrophotometer. The concentration of substrate and metabolites produced was quantified by means of liquid chromatography in Waters 1525/2695 equipment with a differential refractive index detector and Rezex ROA Organic Acid column, with 2.5 mM H$_2$SO$_4$ and a flow rate of 0.5 mL/min. Quantification was performed by means of comparison with standard curves of the products.

REFERENCES

1. Benjaminson M A, de Guzmán B C, and Weil A J. 1963. Voges-Proskauer test: expeditious techniques for routine use. *J. Bacteriol.*, 87: 234-235.
2. Cueto P H, and Méndez B S. 1990. Direct selection of *Clostridium acetobutylicum* fermentation mutants by a proton suicide method. *App. Environ. Microbiol.*, 56: 578-580.
3. Desnuelle P and Naudet M. 1945. Colorimetric determination of acetaldehyde formed on periodate oxidation of 2,3-butanediol. *Bull. Soc. Chim. Fr.* 12:871-8.
4. Nakashimada Y, Kanai K and Nishio N. 1998. Optimization of dilution rate, pH and oxygen supply on optical purity of 2,3-butanediol produced by *Paenibacillus polymyxa* in chemostat culture. *Biotechnol. Lett.* 20: 1133-8.
5. Petrov K and Petrova P. 2009. High production of 2,3-butanediol from glycerol by *Klebsiella pneumonia* G31. *Appl. Microbiol. Biotechnol.* DOI 10.1007/s00253-009-2004-x.
6. Petrov K and Petrova P. 2010. Enhanced production of 2,3-butanediol from glycerol by forced pH fluctuations. *Appl. Microbiol. Biotechnol.* DOI 10.1007/s00253-010-2545-z.
7. Speckman R A and Collins E B. 1982. Specificity of the Westerfeld adaptation of the Voges-Proskauer test. *Appl. Environ. Microbiol.* 44: 40-3.
8. Xiu Z L, and Zeng A P. 2008. Present state and perspective of downstream processing of biological produced 1,3-propanediol and 2,3-butanediol. *Appl. Microbiol. Biotechnol.* DOI 10.1007/s00253-008-1387-4.

The invention claimed is:

1. Mutant strains of the species *Raoultella planticola* that can be used for the production of 2,3-butanediol from glycerol obtained by randomly induced mutagenesis of the *Raoultella planticola* strain CECT843 and subsequent selection in bromate/bromide plates, wherein said mutant strains consist of *R. planticola*, with accession number CECT8158 and accession number CECT8159, deposited in the Spanish Type Culture Collection (CECT) on Dec. 6, 2012, where said mutant strains have improved 2,3-butanediol production capacity compared to *Raoultella planticola* strain CECT843.

2. An industrially viable method for the biotechnological conversion of glycerol into 2,3-butanediol comprising the following steps:
   a) aerobically fermenting the strains according to the claim 1 in a medium comprising an aqueous solution of glycerol under conditions suitable for producing 2,3-butanediol; and b) separating the 2,3-butanediol produced from the reaction medium.

3. The method according to claim 2, wherein the aqueous solution of glycerol contains at least 3% by weight of glycerol.

4. The method according to claim 3, wherein the aqueous solution of glycerol contains at least 6% by weight of glycerol.

5. The method according to claim 2, wherein the reaction temperature of fermentation step a) is 28° C.-37° C.

6. The method according to claim 2, wherein the reaction time of fermentation step a) is 12 to 48 hours.

7. The method according to claim 2, wherein the reaction pH of fermentation step a) is 7.5 to 5.5.

8. The method according to claim 2, wherein the separation of 2,3-butanediol in step b) is done by filtration or centrifugation and subsequent extraction.

9. A method for producing mutant strains of the species *R. planticola* that can be used for the production of 2,3-butanediol from glycerol, comprising randomly induced mutagenesis of the *R. planticola* strain CECT843 and subsequent selection in bromate/bromide plates of mutants with an improved 2,3-butanediol production capacity compared to *Raoultella planticola* strain CECT843.

10. The method according to claim 9, wherein the step of randomly induced mutagenesis is performed by means of a chemical mutagen or UV radiation.

11. The method according to claim 10, wherein the step of random mutagenesis with chemical mutagen is performed by incubating the *R. planticola* strain CECT 843 in a culture medium with 30 g/L of glycerol and 10 µl/mL of ethyl methanesulfonate (EMS) for 1 hour at 30° C.

12. The method according to claim 9, wherein the subsequent selection of mutant strains is done by seeding and incubating the colonies resulting from the mutagenesis step in selection plates with 100 mM NaBr and 100 mM $NaBrO_3$ for 2 to 3 days at pH 6.

13. The method according to claim 12, wherein colonies reducing the pH of the medium below 6.4 are discarded in the selection of mutant strains.

* * * * *

```
                        SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
agagtttgat ymtggctcag                                              20

<210> SEQ ID NO 2
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 2
cakaaaggag gtgatcc                                                 17

<210> SEQ ID NO 3
<211> LENGTH: 1042
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (15)..(17)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (968)..(968)
<223> OTHER INFORMATION: n is a, c, g, or t
<220> FEATURE:
<221> NAME/KEY: misc_feature
<222> LOCATION: (970)..(970)
<223> OTHER INFORMATION: n is a, c, g, or t
```

```
<220> FEATURE:
<221> NAME/KEY: misc_feature
<222> LOCATION: (1001)..(1001)
<223> OTHER INFORMATION: n is a, c, g, or t
<220> FEATURE:
<221> NAME/KEY: misc_feature
<222> LOCATION: (1003)..(1004)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t
<220> FEATURE:
<221> NAME/KEY: misc_feature
<222> LOCATION: (1027)..(1027)
<223> OTHER INFORMATION: n is a, c, g, or t
<220> FEATURE:
<221> NAME/KEY: misc_feature
<222> LOCATION: (1039)..(1039)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t

<400> SEQUENCE: 3
nnnnnnnnnn nnnannntgc agtcgagcgg tagcacagag agcttgctct cgggtgacga      60
gcggcggacg ggtgagtaat gtctgggaaa ctgcctgatg gaggggggata actactggaa    120 cggtagctaa taccgcataa cgtcgcaaga ccaaagtggg ggaccttcgg gcctcatgcc    180
atcagatgtg cccagatggg attagctagt aggtggggta atggctcacc taggcgacga    240
tccctagctg gtctgagagg atgaccagcc acactggaac tgagacacgg tccagactcc    300
tacgggaggc agcagtgggg aatattgcac aatgggcgca agcctgatgc agccatgcgc    360
gtgtatgaag aaggccttcg ggttgtaaag tactttcagc gaggaggaag gcgttaaggt    420
taataacctt agcgattgac gttactcgca gaagaagcac cggctaactc cgtgccagca    480
gccgcggtaa tacggagggt gcaagcgtta atcggaatta ctgggcgtaa agcgcacgca    540
ggcggtttgt taagtcagat gtgaaatccc cgggctcaac ctgggaactg catttgaaac    600
tggcaagctt gagtcttgta gagggggggta gaattccagg tgtagcggtg aaatgcgtag    660
agatctggag gaataccggt ggcgaaggcg gcccctgga caaagactga cgctcagtgc      720
gaaagcgtgg ggagcaaaca ggattagata ccctggtagt ccacgctgta aacgatgtcg    780
acttggaggt tgttcccttg aggagtggct tccggagcta acgcgttaag tcgaccgcct    840
ggggagtacg gncgcaaggt taaaactcaa atgaattgac ggggcccgc acaagggtgg     900 agcatgtggt ttaattcgat gcaacgcgaa gaaccttacc tactcttgac ntccagagaa    960
cttagcanan atgctttggt gccttcggga actctgagac ngnngctgca tggntgncgt   1020
cagctcntgt gtgaatgtng nt                                             1042
```